(12) United States Patent
Hodges et al.

(10) Patent No.: US 7,431,814 B2
(45) Date of Patent: *Oct. 7, 2008

(54) ELECTROCHEMICAL CELL

(75) Inventors: Alastair Hodges, Blackburn South (AU); Thomas W. Beck, North Richmond (AU); Oddvar Johansen, Mulgrave (AU); Ian Andrew Maxwell, Five Dock (AU)

(73) Assignee: LifeScan, Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/843,956

(22) Filed: May 12, 2004

(65) Prior Publication Data

US 2004/0206636 A1    Oct. 21, 2004

Related U.S. Application Data

(63) Continuation of application No. 09/840,624, filed on Apr. 23, 2001, now Pat. No. 6,863,801, which is a continuation of application No. 09/709,968, filed on Nov. 10, 2000, now Pat. No. 6,521,110, which is a continuation of application No. 09/314,251, filed on May 18, 1999, now Pat. No. 6,174,420, which is a continuation-in-part of application No. 09/068,828, filed on Mar. 15, 1999, now Pat. No. 6,179,979, and a continuation-in-part of application No. 08/852,804, filed on May 7, 1997, now Pat. No. 5,942,102.

(30) Foreign Application Priority Data

Nov. 16, 1995   (AU) ..................................... PN6619
Nov. 15, 1996   (AU) ...................... PCT/AU96/00724

(51) Int. Cl.
    *G01N 27/427*    (2006.01)
(52) U.S. Cl. ............................. 204/403.02; 204/403.04

(58) Field of Classification Search ................................
    204/403.01–403.14, 416–418
    See application file for complete search history.

(56) References Cited

U.S. PATENT DOCUMENTS 4,053,381 A    10/1977   Hamblen et al.

(Continued)

FOREIGN PATENT DOCUMENTS

AU    A 54873/94    2/1993

(Continued)

OTHER PUBLICATIONS

Oglesby et al. Anal. Chem. vol. 37, No. 11, Oct. 1965, pp. 1312-1316.*

(Continued)

*Primary Examiner*—Alex Noguerola
(74) *Attorney, Agent, or Firm*—Nutter McClennen & Fish LLP (57) ABSTRACT

A biosensor for use in determining a concentration of a component in an aqueous liquid sample is provided including: an electrochemical cell having a first electrically resistive substrate having a thin layer of electrically conductive material, a second electrically resistive substrate having a thin layer of electrically conductive material, the substrates being disposed with the electrically conductive materials facing each other and being separated by a sheet including an aperture, the wall of which aperture defines a cell wall and a sample introduction aperture whereby the aqueous liquid sample may be introduced into the cell; and a measuring circuit.

14 Claims, 3 Drawing Sheets

U.S. PATENT DOCUMENTS

| | | | |
|---|---|---|---|
| 4,076,596 A | 2/1978 | Connery et al. | |
| 4,088,448 A | 5/1978 | Lilja et al. | |
| 4,224,125 A | 9/1980 | Nakamura et al. | 204/195 B |
| 4,233,029 A | 11/1980 | Columbus | 23/230 R |
| 4,254,083 A | 3/1981 | Columbus | 422/55 |
| 4,254,546 A | 3/1981 | Ullery, Jr. | |
| 4,259,165 A | 3/1981 | Miyake | 204/415 |
| 4,301,412 A | 11/1981 | Hill et al. | 324/442 |
| 4,301,414 A | 11/1981 | Hill et al. | 324/446 |
| 4,303,887 A | 12/1981 | Hill et al. | 324/441 |
| 4,307,188 A | 12/1981 | White | 435/4 |
| 4,319,969 A | 3/1982 | Oda et al. | |
| 4,374,013 A | 2/1983 | Enfors | 204/195 |
| 4,404,066 A | 9/1983 | Johnson | 205/778 |
| 4,431,004 A | 2/1984 | Bessman et al. | 128/635 |
| 4,431,507 A | 2/1984 | Nankai et al. | |
| 4,508,613 A | 4/1985 | Busta et al. | 128/635 |
| 4,517,287 A | 5/1985 | Scheibe et al. | 435/4 |
| 4,517,291 A | 5/1985 | Seago | 435/14 |
| 4,533,440 A | 8/1985 | Kim | 204/1 |
| 4,545,382 A | 10/1985 | Higgins et al. | 128/635 |
| 4,552,840 A | 11/1985 | Riffer | 205/778 |
| 4,554,064 A | 11/1985 | McClintock et al. | |
| 4,591,550 A | 5/1986 | Hafeman et al. | |
| 4,629,563 A | 12/1986 | Wrasidlo | 210/500.34 |
| 4,654,197 A | 3/1987 | Lilja et al. | 422/56 |
| 4,664,119 A | 5/1987 | Bessman et al. | 204/415 |
| 4,711,245 A | 12/1987 | Higgins et al. | 128/635 |
| 4,774,039 A | 9/1988 | Wrasidlo | 264/41 |
| 4,782,265 A | 11/1988 | Schaper et al. | |
| 4,790,925 A | 12/1988 | Miller et al. | 204/415 |
| 4,897,173 A | 1/1990 | Nankai et al. | |
| 4,900,424 A | 2/1990 | Birth et al. | 204/409 |
| 4,911,794 A | 3/1990 | Parce et al. | |
| 4,919,770 A | 4/1990 | Preidel et al. | 204/153.1 |
| 4,963,815 A | 10/1990 | Hafeman | 205/777.5 |
| 4,988,429 A | 1/1991 | Matthiessen et al. | |
| 4,989,452 A | 2/1991 | Toon et al. | |
| 5,059,908 A | 10/1991 | Mina | 324/444 |
| 5,064,516 A | 11/1991 | Rupich | 204/415 |
| 5,089,112 A | 2/1992 | Skotheim et al. | |
| 5,089,320 A | 2/1992 | Straus et al. | |
| 5,095,407 A | 3/1992 | Kanezawa et al. | |
| 5,108,564 A | 4/1992 | Szuminsky et al. | |
| 5,120,420 A | 6/1992 | Nankai et al. | 204/403 |
| 5,122,244 A | 6/1992 | Hoenes et al. | 204/153.1 |
| 5,126,034 A | 6/1992 | Carter et al. | 204/403 |
| 5,128,015 A | 7/1992 | Szuminsky et al. | 205/782.5 |
| 5,141,868 A | 8/1992 | Shanks et al. | 435/288 |
| 5,151,166 A | 9/1992 | Harral et al. | 204/425 |
| 5,156,972 A | 10/1992 | Issachar et al. | |
| 5,171,689 A | 12/1992 | Kawaguri et al. | |
| 5,192,415 A | 3/1993 | Yoshioka et al. | 204/403 |
| 5,229,282 A | 7/1993 | Yoshioka et al. | 435/177 |
| 5,243,516 A | 9/1993 | White | |
| 5,243,526 A | 9/1993 | Ito et al. | |
| 5,269,903 A | 12/1993 | Ikariyama et al. | |
| 5,272,087 A | 12/1993 | El Murr et al. | 435/291 |
| 5,282,950 A | 2/1994 | Dietze et al. | |
| 5,312,590 A | 5/1994 | Gunasingham | |
| 5,314,605 A | 5/1994 | Matthiessen et al. | |
| 5,320,732 A | 6/1994 | Nankai et al. | 204/403 |
| 5,366,609 A | 11/1994 | White et al. | |
| 5,382,346 A | 1/1995 | Uenoyama et al. | 204/403 |
| 5,384,028 A | 1/1995 | Ito | 204/403 |
| 5,385,846 A | 1/1995 | Kuhn et al. | 436/70 |
| 5,388,163 A | 2/1995 | Elko et al. | |
| 5,393,399 A | 2/1995 | Van den Berg et al. | 204/412 |
| 5,395,504 A | 3/1995 | Saurer et al. | |
| 5,399,256 A | 3/1995 | Bohs et al. | |
| 5,413,690 A | 5/1995 | Kost et al. | 204/403 |
| 5,437,999 A | 8/1995 | Diebold et al. | 435/288 |
| 5,443,710 A | 8/1995 | Broderick | |
| 5,496,453 A | 3/1996 | Uenoyama et al. | |
| 5,508,171 A | 4/1996 | Walling et al. | 205/777.5 |
| 5,509,410 A | 4/1996 | Hill et al. | 128/637 |
| 5,512,159 A | 4/1996 | Yoshioka et al. | |
| 5,517,313 A | 5/1996 | Colvin, Jr. | |
| 5,518,590 A | 5/1996 | Fang | |
| 5,520,787 A | 5/1996 | Hanagan et al. | 204/409 |
| 5,527,446 A | 6/1996 | Kosek et al. | 204/415 |
| 5,567,302 A | 10/1996 | Song et al. | 205/777.5 |
| 5,575,895 A | 11/1996 | Ikeda et al. | |
| 5,607,565 A | 3/1997 | Azarnia et al. | |
| 5,611,908 A | 3/1997 | Matthiessen et al. | 205/775 |
| 5,620,579 A | 4/1997 | Genshaw et al. | 205/775 |
| 5,628,890 A | 5/1997 | Carter et al. | 204/403 |
| 5,645,709 A | 7/1997 | Birch et al. | 205/775 |
| 5,651,869 A | 7/1997 | Yoshioka et al. | |
| 5,682,884 A | 11/1997 | Hill et al. | |
| 5,695,947 A | 12/1997 | Guo et al. | |
| 5,726,565 A | 3/1998 | Uchiyama et al. | |
| 5,727,548 A | 3/1998 | Hill et al. | |
| 5,762,770 A | 6/1998 | Pritchard et al. | |
| 5,849,174 A | 12/1998 | Sanghera et al. | |
| 5,863,400 A | 1/1999 | Drummond et al. | |
| 5,909,114 A | 6/1999 | Uchiyama et al. | |
| 5,942,102 A | 8/1999 | Hodges et al. | |
| 5,997,817 A | 12/1999 | Crismore et al. | 422/58 |
| 6,071,391 A * | 6/2000 | Gotoh et al. | 204/403.05 |
| 6,117,289 A | 9/2000 | Yamamoto et al. | |
| 6,153,069 A | 11/2000 | Pottgen et al. | |
| 6,174,420 B1 | 1/2001 | Hodges et al. | 204/403.11 |
| 6,179,979 B1 * | 1/2001 | Hodges et al. | 204/403.06 |
| 6,193,873 B1 | 2/2001 | Ohara et al. | |
| 6,214,205 B1 | 4/2001 | Willner et al. | |
| 6,218,134 B1 | 4/2001 | Yamauchi et al. | |
| 6,270,637 B1 | 8/2001 | Crismore et al. | |
| 6,284,125 B1 | 9/2001 | Hodges et al. | |
| 6,325,973 B1 | 12/2001 | Leland et al. | |
| 6,413,395 B1 | 7/2002 | Bhullar et al. | |
| 6,413,410 B1 | 7/2002 | Hodges et al. | |
| 6,461,496 B1 | 10/2002 | Feldman et al. | |
| 6,503,381 B1 | 1/2003 | Gotoh et al. | |
| 6,521,110 B1 | 2/2003 | Hodges et al. | |
| 6,521,260 B1 | 2/2003 | Staniforth | |
| 6,544,212 B2 | 4/2003 | Galley et al. | |
| 6,780,756 B1 | 8/2004 | Farber et al. | |
| 6,863,801 B2 | 3/2005 | Hodges et al. | |
| 2002/0012943 A1 | 1/2002 | Fowlkes et al. | |

FOREIGN PATENT DOCUMENTS

| | | |
|---|---|---|
| AU | A 31042/93 | 7/1993 |
| DE | 3103 464 | 8/1982 |
| DE | 3103 464 A1 | 8/1982 |
| DE | 297 09 141 | 8/1997 |
| EP | 0125137 | 11/1984 |
| EP | 0 170 375 | 2/1986 |
| EP | 0170375 B1 | 2/1986 |
| EP | 0 251 915 A2 | 1/1988 |
| EP | 0 255 291 A1 | 2/1988 |
| EP | 0 266 204 A2 | 4/1988 |
| EP | 0 278 647 A2 | 8/1988 |
| EP | 0290770 | 11/1988 |
| EP | 0 299 779 A2 | 1/1989 |
| EP | 0359 831 A1 | 10/1989 |
| EP | 0 351 516 A2 | 1/1990 |
| EP | 0 351 891 (A2) | 1/1990 |
| EP | 0 351 892 A2 | 1/1990 |
| EP | 0 351 892 (A2) | 1/1990 |
| EP | 0351891 A2 | 1/1990 |
| EP | 0 171 375 A1 | 5/1990 |
| EP | 0367432 | 5/1990 |

| | | |
|---|---|---|
| EP | 0 400 918 A1 | 12/1990 |
| EP | 0406304 B1 | 1/1991 |
| EP | 0 418 404 A1 | 3/1991 |
| EP | 0422708 | 4/1991 |
| EP | 0 451 981 A2 | 10/1991 |
| EP | 0 127 958 (A2) | 3/1992 |
| EP | 0 560 336 A1 | 9/1993 |
| EP | 0593096 | 4/1994 |
| EP | 0603954 | 6/1994 |
| EP | 0609760 A1 | 8/1994 |
| EP | 0359831 | 8/1995 |
| EP | 0735303 | 10/1996 |
| EP | 0741186 | 11/1996 |
| EP | 0764469 | 3/1997 |
| EP | 0964059 | 12/1999 |
| EP | 0 585 933 | 12/2005 |
| GB | 2020424 A | 11/1979 |
| GB | 2 154735 A | 9/1985 |
| GB | 2 194 112 | 2/1988 |
| GB | 2 201248 | 8/1988 |
| GB | 2215846 | 9/1989 |
| GB | 2 235 050 A | 2/1991 |
| JP | 54006595 | 1/1979 |
| JP | 60-017344 | 1/1985 |
| JP | 60-250246 | 12/1985 |
| JP | 60244853 | 12/1985 |
| JP | 60250246 | 12/1985 |
| JP | 61-002060 | 1/1986 |
| JP | 62-228274 | 10/1987 |
| JP | 01-253648 | 10/1989 |
| JP | 01-294453 | 11/1989 |
| JP | 3-167464 | 7/1991 |
| JP | 4-66112 | 3/1992 |
| JP | 04343065 | 11/1992 |
| JP | 05002007 | 1/1993 |
| JP | 05-80018 | 3/1993 |
| JP | H5-312761 | 11/1993 |
| JP | 6222874 | 8/1994 |
| JP | 06-310746 | 11/1994 |
| JP | 08062179 | 3/1996 |
| JP | 08304340 | 11/1996 |
| JP | 09-222408 | 8/1997 |
| JP | 09-236570 | 9/1997 |
| JP | 09-243588 | 9/1997 |
| JP | 2007225619 | 9/2007 |
| RU | 2046361 C1 | 10/1995 |
| SU | 1351627 | 11/1987 |
| SU | 1806187 | 3/1993 |
| WO | WO89/08713 | 9/1989 |
| WO | WO-89/08713 | 9/1989 |
| WO | 9005910 | 5/1990 |
| WO | 9109139 | 6/1991 |
| WO | WO-92/15701 | 9/1992 |
| WO | WO-94/02842 | 2/1994 |
| WO | WO-94/29731 | 12/1994 |
| WO | WO-95/16198 | 6/1995 |
| WO | WO-95/21934 | 8/1995 |
| WO | WO95/28634 | 10/1995 |
| WO | WO97/00441 | 1/1997 |
| WO | WO-97/18464 | 5/1997 |
| WO | WO97/18465 | 5/1997 |
| WO | WO-97/18465 | 5/1997 |
| WO | WO-98/11426 | 9/1998 |
| WO | WO-98/43073 | 10/1998 |
| WO | WO-98/43074 | 10/1998 |
| WO | WO-99/46585 | 9/1999 |
| WO | WO-0020626 A1 | 4/2000 |
| WO | WO-02/08763 | 1/2002 |

OTHER PUBLICATIONS (Abstract Only) Miyawaki Akiyoshi et al, *Measurement Using Biosensor*, JP 60250246, Dec. 10, 1985.

John F. Cassidy et al., "Novel Electrochemical Device for the Detection of Cholesterol or Glucose" in *Analyst* Apr. 1993, vol. 118, p. 415-18.

Derwent Abstract Accession No. 93-140898/17, JP, A., 05080018 (Rikagaku Kenkyusho) Mar. 30, 1993.

Derwent Abstract Accession No. 95-026336/04, JP, A., 06310746 (Hitachi Ltd) Nov. 4, 1994.

Simultaneous Determination of Diffusion Coefficient and Concentration by Chronoaperometry at a Microdisk Electrode; Jung et al.: *Bull. Korean Chem. Soc.*, 1994, vol. 15, No. 3, 209-213.

Diagnostic Criteria For The Study Of Chemical And Physical Processes By Twin-Electrode Thin-Layer Electrochemistry; Anderson et al., *J. Electroanal. Chem*, 12(996)477-494.

Paeschke, M. et al., "Dynamic Redox Recycling of Cytochrome C", *Journal of Electroanalytical Chemistry*, vol. 393, No. 1/02, 1995, pp. 131-135.

Paeschke, M. et al., "Properties of Interdigital Electrode Arrays With Different Geometries", *Analytica Chimica Acta*; vol. 305, No. 1/03, 1995, pp. 126-136.

Yaoita, M. et al., "Pulse Chronoamperometric Technique of Enzyme Embodied Electrode Applied to Glucose Measurement in Whole Serum", *Extended Abstracts, US Electrochemical Society*, Princeton, NJ; vol. 93/1, 1993, p. 2801.

Hall, E., *Biosensors*, Chapter 5: "Amperometric Assay Techniques", 1990.

Denuault, G. et al., "Direct Determination of Diffusion-Coefficients by Chronoamperometry at Microdisk Electrodes", *Journal of Electroanalytical Chemistry*, vol. 308, No. 1-2, 1991, pp. 27-38.

Seddon, B. J., et al., "Preparation and Amperometric Response of Carbon and Platimun Dual Cylinder Microelectrodes", *Electrochinica Act*, vol. 40, No. 4, Mar. 1, 1995, pp. 455-465.

Derwent Abstracts Accession No. 92 119462/15, Class S03, JP, A, 04-62463 (Tokyo Yogyo K.K.) Feb. 27, 1992. Patent Abstracts of Japan.

Patent Abstracts of Japan, p-269, p. 168, JP, A, 59-3345, (Hitachi Seisakusho K.K.) Jan. 10, 2994.

Laszlo Daruhazi et al., "Cyclic Voltammetry for Reversible Redox-Electrode Reaction in Thin Layer Cells with Closely Separated Working and Auxiliary Electrodes of the Same Size", in J. Electroanal. Chem. 264: 77-89 (1989).

(Abstract Only) Kobayashi Yoshiaki et al., *Biosensor*, JP 61002060, A; Jan. 3, 1986.

European Search Report, Application No. 96937919.

European Search Report, Application No. EP 99202305.

JPO Patent Abstract of JP-04-56112-A.

Patent Abstract of Japan, Publication No. 60250246, published Dec. 10, 1985.

Abstract for JP 6310746 A; To: Miyahara et al.

Hubbard, et al., The Theory and Practice of Electrochemistry with Thin Layer Cells, *Electroanalytical Chemistry*, (Bard, Ed.), Marcel Deletier, New York, 1970, vol. 4., pp. 129-214.

Specification sheet from Adhesives Research, Inc. Arclad®8314 (May 2, 1997).

Niwa, O., et al., "Electrochemical Behavior of Reversible Redox Species at Interdigitated Array Electrodes with Different Geometries: Consideration of Redox Cycling and Collection"; Analytical Chemistry, Mar. 1990, vol. 62, No. 5.

Data Sheet for ARcae 7148 double-side adhesive coated polyester film, (Mar. 30, 1995) (2 pp.).

Reilly, Charles: "Electrochemistry Using Thin-layer Cells": Rev. Pure and Appl. Chem. vol. 18.

Christensen & Anson; "Chronpotentionmetry in Thin Layers of Solution"; Analytical Chemistry; vol. 35; No. 2, 1963.

Hubbard & Anson; "New Electrodes for Chronopotentiometry in Thin Layers of Solutions"; Analytical Chemistry; vol. 36, No. 4, Apr. 1964.

McDuffie, Anderson, & Reilly; "Twin Electrode Thin-Layer Electrochemsitry"; Analytical Chemistry; vol. 38; No. 7; pp. 883-890, Jun. 1966.

Morris, Franta and White: "Electrochemistry at Pt Band Electrodes of Width Approaching Molecular Dimensions. Breakdown of Transport Equations at Very Small Electrodes"; The Journal of Physical Chemistry; vol. 91, No. 13; 1987.

Nicholson and Shain; "Theoty of Stationary Electrode Polarography"; Analytical Chemistry; vol. 36, No. 4, Apr. 1964.

Pickup, Lutner, Leidner, and Murray; "Redox Conduction in Single and bilayer Films of Redox Polymer"; American Chemical Society; vol. 106; No. 7; 1984.

Chidsey, Feldman, Lundgren, and Murray; "Micrometer-Spaced Platinum Interdigitated Array Electrode: Fabrication, Theory, and Initial Use"; Analytical Chemistry; vol. 58, No. 3; Mar. 1986.

Hubbard: "Study of the Kinetics of Electrochemical Reactions by Thin-Layer Voltammetry"; Journal of Electroanalytical Chemistry; vol. 22; 1969.

Anderson and Reilly; "Thin-Layer Electrochemistry: Steady-State Methods of Studying Rate Processes"; J. Electroanal. Chem., vol. 10; 1965.

Abstracts of Jpan; Title: "Electrolyte Analyzer"; Publication No. 08062179A; Mar. 8, 1996.

Uchiyama et al., Measurement Of Homogeneous Reaction Rate By Concentration-Step, Controlled Potential Electrolysis,: *J. Electroanal. Chem Interfacial Electrochem.*, 91(3):301-308, 1978.

Trojanek et al., "Data processing in reaction rate measurements," *Collect. Chezech, Chem commun.*, 38(9):2572-2580, 1973.

O. Niwa, M. Morita, H. Tabei, "Highly Selective Electrochemical Detection of Dopamine Using Interdigital Array of Electrodes Modified with Nafion/Polyester Ionomer Layered Film", Electroanalysis, vol. 6, No. 3, Mar. 1994, pp. 237-243, XP000943528.

J. Salbeck, "Spectrochemical Thin-Layer Cell for Nanaqueous Solvent Systems," *Anal. Chem.*, 1993, vol. 65, pp. 2165-2173.

Anderson, McDuffie and Reilley; *"Diagnostic Criteria for the Study of Chemical and Physical Processes by Twin-Electrode Thin-Layer Electrochemistry"*; Electroanalytical Chemistry; vol. 12, 1966, pp. 477-494.

European Search Report No. EP 03007604 dated May 19, 2003.

Patent Abstracts of Japan, JP A 04-62463.

Patent Abstract of Japan JP63-139246 A2 (Jun. 1988).

Enthone - Imaging Technologies Update Jun. 2001/No. 3) Enplate DSR 3241.

International Search Report PCT/US02/31289 dated Jul. 18, 2003.

Vidal, J. C. et al., "A Chronoamperometric Sensor for Hydrogen Peroxide Based on Electron Transfer Between Immobilized Horseradish Peroxidase on a Glassy Carbon Electrode and a Diffusing Ferrocene Mediator", Sensors and Actuators B:Chemical, vol. 21, Issue 2, Aug. 1994, pp. 135-141.

* cited by examiner

ELECTROCHEMICAL CELL

RELATED APPLICATIONS

This application is a continuation of U.S. patent application Ser. No. 09/840,624 filed on Apr. 23, 2001, which issued as U.S. Pat. No. 6,863,801 on Mar. 8, 2005, which is a continuation of U.S. application Ser. No. 09/709,968, filed Nov. 10, 2000, which issued as U.S. Pat. No. 6,521,110 on Feb. 18, 2003, which is a continuation of U.S. application Ser. No. 09/314,251, filed May 18, 1999, which issued as U.S. Pat. No. 6,174,420 on Jan. 16, 2001, which is a continuation-in-part of U.S. application Ser. No. 09/068,828, filed on Mar. 15, 1999, which issued as U.S. Pat. No. 6,179,979 on Jan. 30, 2001, and is also a continuation-in-part of U.S. application Ser. No. 08/852,804, filed on May 7, 1997, which issued as U.S. Pat. No. 5,942,102 on Aug. 24, 1999, the contents of which are incorporated herein by reference in their entirety.

FIELD OF THE INVENTION

This invention relates to an electrochemical cell for determining the concentration of an analyte in a carrier.

BACKGROUND OF THE INVENTION

The invention herein described is an improvement in or modification of the invention described in our co-pending U.S. application Ser. No. 08/981,385, entitled ELECTROCHEMICAL CELL, filed on Dec. 18, 1997, the contents of which are incorporated herein by reference in its entirety.

The invention will herein be described with particular reference to a biosensor adapted to measure the concentration of glucose in blood, but it will be understood not to be limited to that particular use and is applicable to other analytic determinations.

It is known to measure the concentration of a component to be analysed in an aqueous liquid sample by placing the sample into a reaction zone in an electrochemical cell comprising two electrodes having an impedance which renders them suitable for amperometric measurement. The component to be analysed is allowed to react directly or indirectly with a redox reagent whereby to form an oxidisable (or reducible) substance in an amount corresponding to the concentration of the component to be analysed. The quantity of the oxidisable (or reducible) substance present is then estimated electrochemically. Generally this method requires sufficient separation of the electrodes so that electrolysis products at one electrode cannot reach the other electrode and interfere with the processes at the other electrode during the period of measurement.

In our co-pending application we described a novel method for determining the concentration of the reduced (or oxidised) form of a redox species in an electrochemical cell of the kind comprising a working electrode and a counter (or counter/reference) electrode spaced from the working electrode by a predetermined distance. The method involves applying an electric potential difference between the electrodes and selecting the potential of the working electrode such that the rate of electro-oxidation of the reduced form of the species (or of electro-reduction of the oxidised form) is diffusion controlled. The spacing between the working electrode and the counter electrode is selected so that reaction products from the counter electrode arrive at the working electrode. By determining the current as a function of time after application of the potential and prior to achievement of a steady state current and then estimating the magnitude of the steady state current, the method previously described allows the diffusion coefficient and/or the concentration of the reduced (or oxidised) form of the species to be estimated.

Our co-pending application exemplifies this method with reference to use of a "thin layer electrochemical cell" employing a GOD/Ferrocyanide system. As herein used, the term "thin layer electrochemical cell" refers to a cell having closely spaced electrodes such that reaction product from the counter electrode arrives at the working electrode. In practice, the separation of electrodes in such a cell for measuring glucose in blood will be less than 500 microns, and preferably less than 200 microns.

The chemistry used in the exemplified electrochemical cell is as follows:

glucose+GOD→gluconic acid+GOD*   reaction 1

GOD*+2ferricyanide→GOD+2ferrocyanide   reaction 2 where GOD is the enzyme glucose oxidase, and GOD* is the 'activated' enzyme. Ferricyanide ($[Fe(CN)_6]^{3-}$) is the 'mediator' which returns the GOD* to its catalytic state. GOD, an enzyme catalyst, is not consumed during the reaction so long as excess mediator is present. Ferrocyanide ($[Fe(CN)_6]^{4-}$) is the product of the total reaction. Ideally there is initially no ferrocyanide, although in practice there is often a small quantity. After reaction is complete the concentration of ferrocyanide (measured electrochemically) indicates the initial concentration of glucose. The total reaction is the sum of reactions 1 and 2:

reaction 3

$$\text{glucose} + 2\text{ferricyanide} \xrightarrow{\text{GOD}} \text{gluconic acid} + 2\text{ferrocyanide}$$

"Glucose" refers specifically to β-D-glucose.

The prior art suffers from a number of disadvantages. Firstly, sample size required is greater than desirable. It would be generally preferable to be able to make measurements on samples of reduced volume since this in turn enables use of less invasive methods to obtain samples.

Secondly, it would be generally desirable to improve the accuracy of measurement and to eliminate or reduce variations due, for example, to cell asymmetry or other factors introduced during mass production of microcells. Likewise, it would be desirable to reduce electrode "edge" effects.

Thirdly, since the cells are disposable after use, it is desirable that they be capable of mass production at relatively low cost.

SUMMARY OF THE INVENTION

In a first embodiment of the present invention, a biosensor for use in determining a concentration of a component in an aqueous liquid sample is provided, the biosensor including: (a) an electrochemical cell, the electrochemical cell including a first electrically resistive substrate having a first thin layer of a first electrically conductive material on a first face, a second electrically resistive substrate having a second thin layer of a second electrically conductive material on a second face, the substrates being disposed with the first electrically conductive material facing the second electrically conductive material and being separated by a sheet including an aperture, the wall of which aperture cooperates with the electrically conductive materials to define a cell wall, and wherein the aperture defines a working electrode area in the cell, the cell further including a sample introduction aperture whereby the aqueous liquid sample may be introduced into the cell; and (b) a measuring circuit.

In one aspect of the first embodiment, the electrochemical cell further includes a socket region having a first contact area in electrical communication with the first thin layer of the first electrically conductive material and a second contact area in electrical communication with the second thin layer of the second electrically conductive material, whereby the electrochemical cell may be electrically connected with the measuring circuit.

In another aspect of the first embodiment, the measuring circuit includes a tongue plug.

In a further aspect of the first embodiment, at least one of the first electrically conductive material and the second electrically conductive material includes a metal. The metal may further include a sputter coated metal.

In still other aspects of the first embodiment, the aqueous liquid sample includes blood, and the component includes glucose.

In yet another aspect of the first embodiment, the measuring circuit includes an automated instrument for detecting an electrical signal from the electrochemical cell and relating the electrical signal to the concentration of the component in the aqueous liquid sample.

In a further aspect of the first embodiment, the electrochemical cell includes a substantially flat strip having a thickness, the strip having at least two lateral edges, and wherein the sample introduction aperture includes a notch through the entire thickness of the strip in at least one of the lateral edges thereof.

In a second embodiment of the present invention, a biosensor for use in determining a concentration of a component in an aqueous liquid sample is provided, the biosensor including: (a) a thin layer electrochemical cell, the cell including: (i) an electrically resistive sheet including an aperture wherein the aperture defines a working electrode area in the cell; (ii) a first electrode layer covering the aperture on a first side of the sheet; (iii) a second electrode layer covering the aperture on a second side of the sheet; and (iv) a passage for admission into the aperture of the aqueous liquid sample; and (b) a measuring circuit.

In one aspect of the second embodiment, the electrochemical cell further includes a socket region having a first contact area in electrical communication with the first electrode layer and a second contact area in electrical communication with the second electrode layer, whereby the electrochemical cell may be electrically connected with the measuring circuit.

In another aspect of the second embodiment, the measuring circuit includes a tongue plug.

In still other aspects of the second embodiment, the aqueous liquid sample includes blood, and the component includes glucose.

In a further aspect of the second embodiment, the measuring circuit includes an automated instrument for detecting an electrical signal from the electrochemical cell and relating the electrical signal to the concentration of the component in the aqueous liquid sample.

In yet another aspect of the second embodiment, the cell includes a substantially flat strip having a thickness, the strip having at least two lateral edges, and wherein the passage for admission into the aperture includes a notch through the entire thickness of the strip in at least one of the lateral edges thereof.

In a third embodiment of the present invention, an apparatus for determining a concentration of a reduced form or an oxidized form of a redox species in a liquid sample is provided, the apparatus including: (a) a hollow electrochemical cell having a working electrode and a counter or counter/reference electrode wherein the working electrode is spaced from the counter or counter/reference electrode by less than 500 µm; (b) means for applying an electric potential difference between the electrodes; and (c) means for electrochemically determining the concentration of the reduced form or the oxidized form of the redox species in the liquid sample.

In one aspect of the third embodiment, means for electrochemically determining the concentration of the reduced form or the oxidized form of the redox species includes: (i) means for determining a change in current with time after application of the electric potential difference and prior to achievement of a steady state current; (ii) means for estimating a magnitude of the steady state current; and (iii) means for obtaining from the change in current with time and the magnitude of the steady state current, a value indicative of the concentration of the reduced form or the oxidized form of the redox species.

In another aspect of the third embodiment, the cell further includes a socket region having a first contact area in electrical communication with the working electrode and a second contact area in electrical communication with the counter or counter/reference electrode, whereby the cell may be electrically connected with at least one of the means for applying an electric potential difference between the electrodes and the means for electrochemically-determining the concentration of the reduced form or the oxidized form of the redox species in the liquid sample.

In a further aspect of the third embodiment, at least one of the means for applying an electric potential difference between the electrodes and the means for electrochemically determining the concentration of the reduced form or the oxidized form of the redox species in the liquid sample includes a tongue plug.

In yet another aspect of the third embodiment, at least one of the means for applying an electric potential difference between the electrodes and the means for electrochemically determining the concentration of the reduced form or the oxidized form of the redox species in the liquid sample includes an automated instrument for detecting an electrical signal from the electrochemical cell and relating the electrical signal to the concentration of the reduced form or the oxidized form of the redox species in the liquid sample.

In a further aspect of the third embodiment, the cell includes a substantially flat strip having a thickness, the strip having at least two lateral edges, and wherein a notch extends through a wall of the electrochemical cell and through the entire thickness of the strip in at least one of the lateral edges thereof, whereby the liquid sample may be introduced into the cell.

In still other aspects of the third embodiment, the liquid sample includes blood, and the redox species includes glucose.

In a fourth embodiment of the present invention, a method for determining a concentration of a reduced form or an oxidized form of a redox species in a liquid sample is provided, the method including: (a) providing a hollow electrochemical cell having a working electrode and a counter or counter/reference electrode wherein the working electrode is spaced from the counter or counter/reference electrode by less than 500 µm; (b) applying an electric potential difference between the electrodes; and (c) electrochemically determining the concentration of the reduced form or the oxidized form of the redox species in the liquid sample.

In one aspect of the fourth embodiment, step (c) includes: (i) determining a change in current with time after application of the electric potential difference and prior to achievement of a steady state current; (ii) estimating a magnitude of the steady state current; and (iii) obtaining from the change in current with time and the magnitude of the steady state current, a value indicative of the concentration of the reduced form or the oxidized form of the redox species.

In another aspect of the fourth embodiment, the cell further includes a socket region having a first contact area in electrical communication with the working electrode and a second contact area in electrical communication with the counter or counter/reference electrode.

In a further aspect of the fourth embodiment, step (b) further includes the step of: providing an automated instrument for applying an electric potential difference between the electrodes.

In yet another aspect of the fourth embodiment, step (c) includes the steps of: (i) providing an automated instrument for detecting an electrical signal from the electrochemical cell; and (ii) relating the electrical signal to the concentration of the reduced form or the oxidized form of the redox species in the liquid sample.

In a further aspect of the fourth embodiment, the cell includes a substantially flat strip having a thickness, the strip having at least two lateral edges, and wherein a notch extends through a wall of the electrochemical cell and through the entire thickness of the strip in at least one of the lateral edges thereof, whereby the liquid sample may be introduced into the cell.

In still other aspects of the fourth embodiment, the liquid sample includes blood and the redox species includes glucose.

BRIEF DESCRIPTION OF THE DRAWINGS

The invention will now be particularly described by way of example only with reference to the accompanying schematic drawings wherein.

DETAILED DESCRIPTION OF THE PREFERRED EMBODIMENT

The construction of a thin layer electrochemical cell will now be described by way of example of the improved method of manufacture.

Step 1: A sheet 1 of Melinex® (a chemically inert, and electrically resistive Polyethylene Terephthalate ["PET"]) approximately 13 cm×30 cm and 100 micron thick was laid flat on a sheet of release paper 2 and coated using a Number 2 MYAR bar to a thickness of 12 microns wet (approximately 2–5 microns dry) with a water-based heat activated adhesive 3 (ICI Novacoat system using catalyst:adhesive). The water was then evaporated by means of a hot air dryer leaving a contact adhesive surface. The sheet was then turned over on a release paper and the reverse side was similarly coated with the same adhesive 4, dried, and a protective release paper 5 applied to the exposed adhesive surface. The edges were trimmed to obtain a sheet uniformly coated on both sides with tacky contact adhesive protected by release paper.

Figure 1:
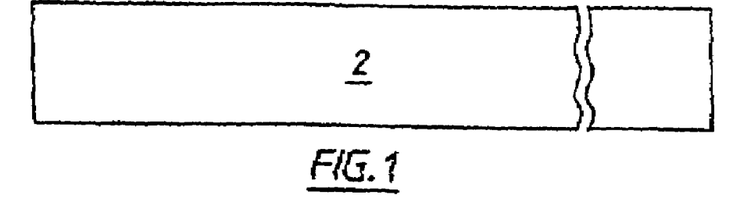
FIG. 1 shows the product of manufacturing step 2 in plan.
Figure 2:
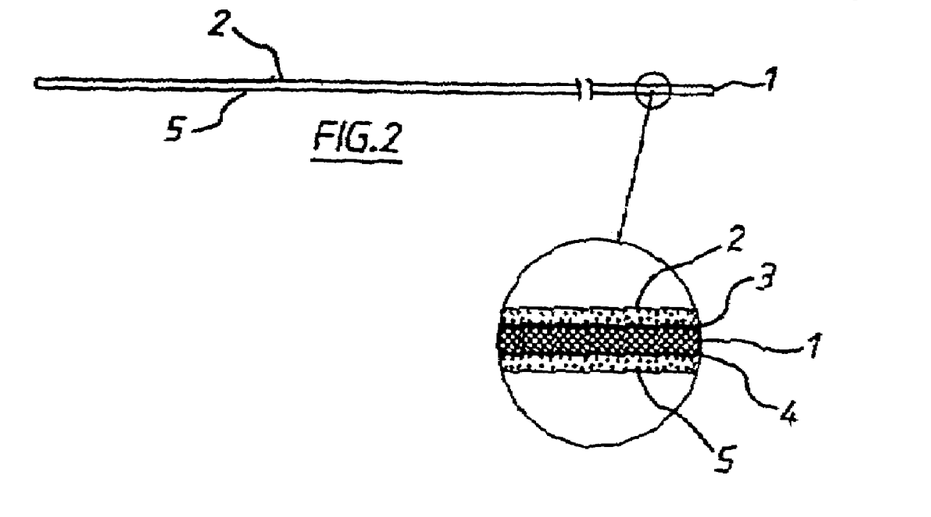
FIG. 2 shows the product of FIG. 1 in side elevation.
Figure 3:
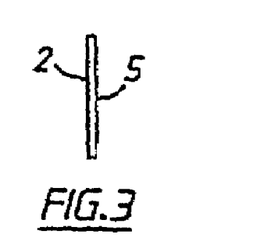
FIG. 3 shows the product of FIG. 1 in end elevation.
Figure 4:
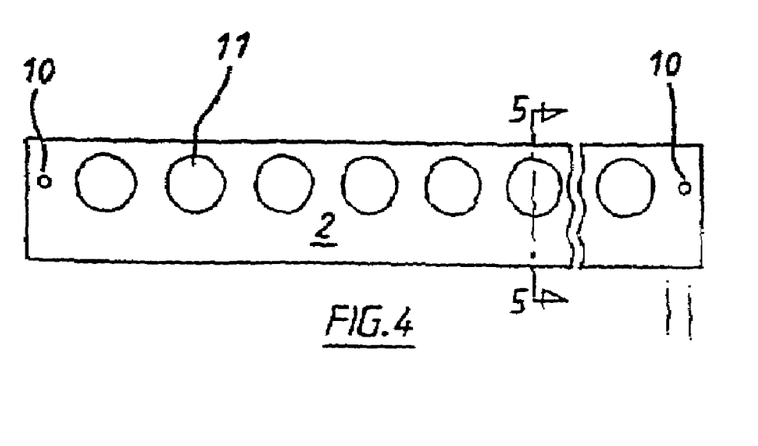
FIG. 4 shows the product of manufacturing step 3 in plan.
Figure 5:
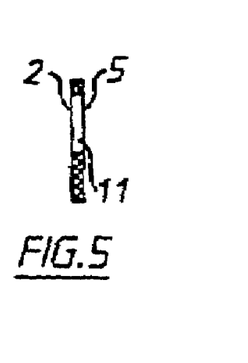
FIG. 5 shows the product of FIG. 4 in cross-section on line 5—5 of FIG. 4.

Step 2: The sheet with protective release papers was cut into strips 7, each about 18 mm×210 mm (FIGS. 1–3).

Step 3: A strip 7 of adhesive-coated PET from step 2 with release paper 2, 5 on respective sides, was placed in a die assembly (not shown) and clamped. The die assembly was adapted to punch the strip with a locating hole 10 at each end and with for example 37 circular holes 11 each of 3.4 mm diameter at 5 mm centres equi-spaced along a line between locating holes 10. The area of each hole 11 is approximately 9 square mm.

Step 4: A sheet 12 of Mylar® PET approximately 21 cm square and 135 microns thick was placed in a sputter coating chamber for palladium coating 13. The sputter coating took place under a vacuum of between 4 and 6 millibars and in an atmosphere of argon gas. Palladium was coated on the PET to a thickness of 100–1000 angstroms. There is thus formed a sheet 14 having a palladium sputter coating 13.

Figure 6:
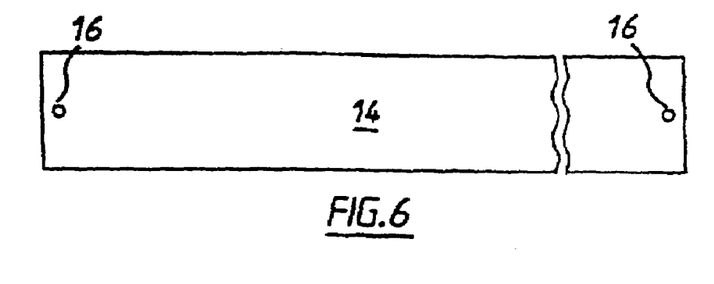
FIG. 6 shows the product of manufacturing step 5 in plan.
Figures 7, 9, 11:
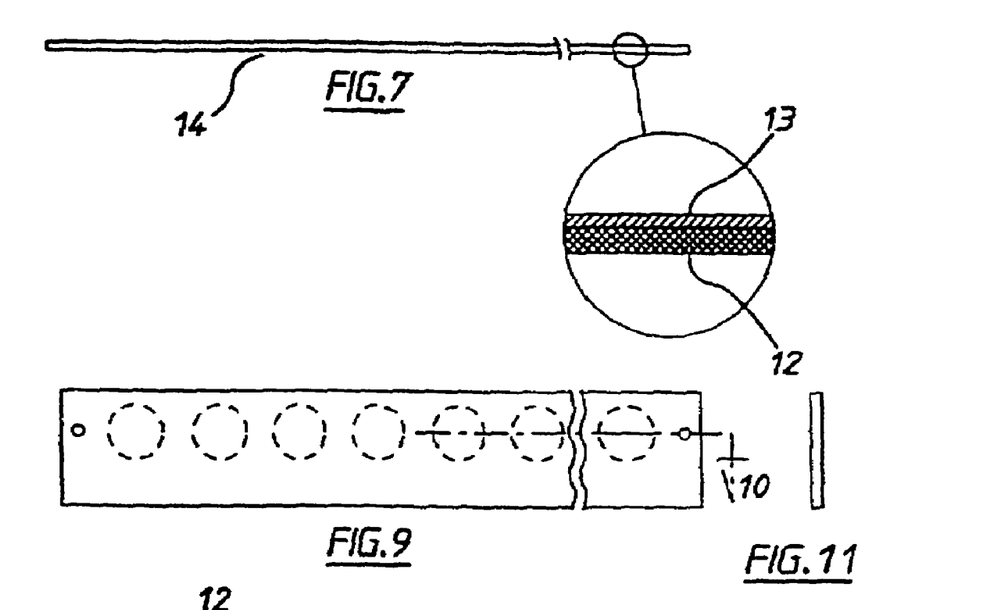
FIG. 7 shows the product of FIG. 6 in side elevation.
FIG. 9 shows the product of manufacturing step 7 in plan.
FIG. 11 shows the product of FIG. 9 in end elevation.
Figure 8:
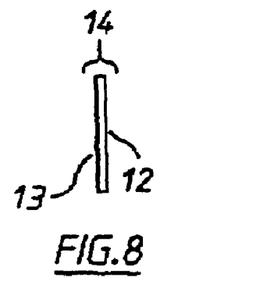
FIG. 8 shows the product of FIG. 6 in end elevation.

Step 5: The palladium coated PET sheet 14 from Step 4 was then cut into strips 14 and 15 and a die was used to punch two location holes 16 in each strip, at one end (FIGS. 6, 7 and 8). Strips 14 and 15 differ only in dimension strips 14 being 25 mm×210 mm and strips 15 being 23 mm×210 mm.

Step 6: A spacer strip 7 prepared as in step 3 was then placed in a jig (not shown) having two locating pins (one corresponding to each locating hole 10 of strip 7) and the upper release paper 2 was removed. A strip 14 of palladium coated PET prepared as in step 5 was then laid over the adhesive layer, palladium surface downwards, using the jig pins to align the locating holes 16 with the underlying PET strip 7. This combination was then passed through a laminator comprising a set of pinch rollers, one of which was adapted to heat the side bearing a palladium coated PET strip 14. The roller on the opposite side of the strip 7 was cooled. By this means, only the adhesive between the palladium of strip 14 and PET strip 7 was activated.

Figure 10:
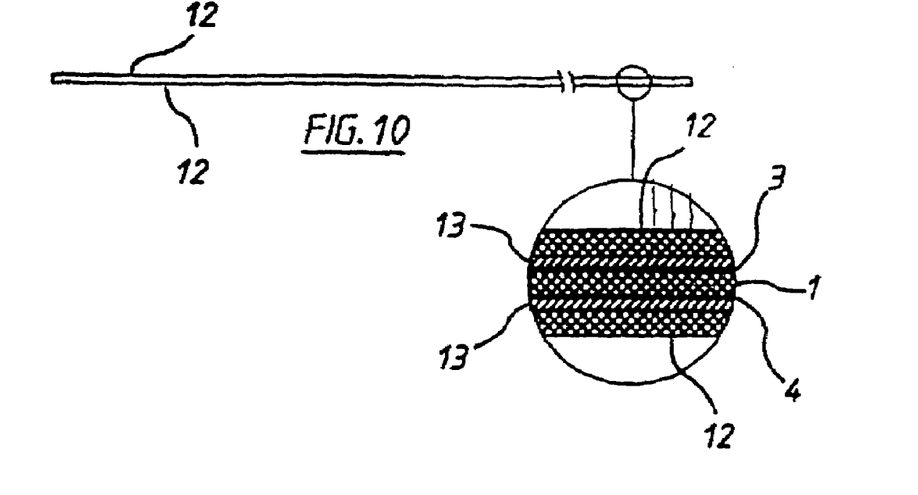
FIG. 10 is a cross-section of FIG. 9 on line 10—10.

Step 7: PET strip 7 was then turned over and located in the jig with the release coating uppermost. The release coating was peeled off and second palladium coated strip 15 was placed palladium side down on the exposed adhesive surface using the locating pins to align the strips. this assembly was now passed again through the laminator of step 6, this time with the hot roll adjacent the palladium coated Mylar® added in step 7 so as to activate the intervening adhesive (FIGS. 9, 10 and 11).

Step 8: The assembly from step 7 was returned to the die assembly and notches 17 punched in locations so as to extend between the circular holes 11 previously punched in the Melinex® PET and the strip edge 17. Notches 16 extend so as to intercept the circumference of each circular cell. The strip was then guillotined to give 37 individual "sensor strips", each strip being about 5 mm wide and each having one thin layer cavity cell (FIGS. 12, 13 and 14).

Figure 12:
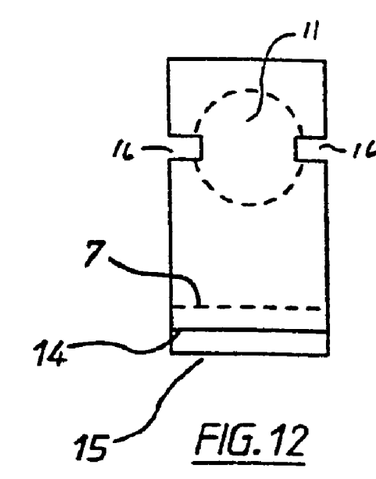
FIG. 12 shows a cell according to the invention in plan.
Figure 13:
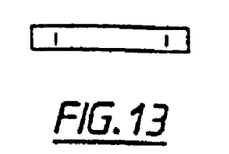
FIG. 13 shows the call of FIG. 12 in side elevation.
Figure 14:
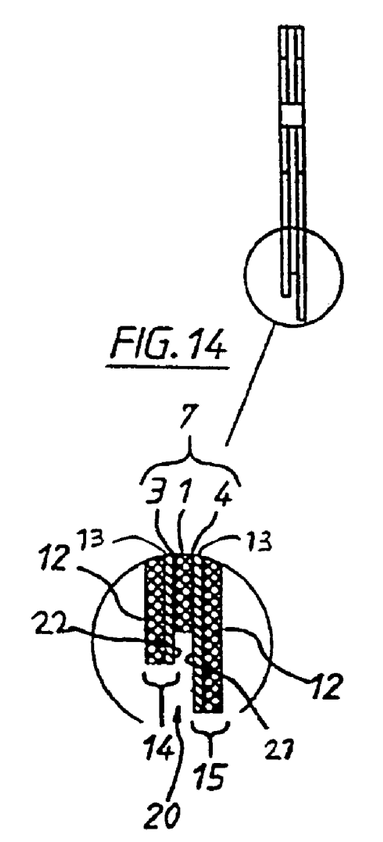
FIG. 14 shows the cell of FIG. 12 in end elevation.

There is thus produced a cell as shown in FIGS. 12, 13 or 14. The cell comprises a first electrode consisting of PET layer 12, a palladium layer 13, an adhesive layer 3, a PET sheet 1, a second adhesive layer 4, a second electrode comprising palladium layer 13, and a PET layer 12. Sheet 1 defines a cylindrical cell 11 having a thickness in the cell axial direction corresponding to the thickness of the Melinex®

PET sheet layer 1 together with the thickness of adhesive layers 3 and 4. The cell has circular palladium end walls. Access to the cell is provided at the side edge of the cell where notches 16 intersect cell 11.

In preferred embodiments of the invention, a sample to be analysed is introduced to the cell by capillary action. The sample is placed on contact with notch 16 and is spontaneously drawn by capillary action into the cell, displaced air from the cell venting from the opposite notch 16. A surfactant may be included in the capillary space to assist in drawing in the sample.

The sensors are provided with connection means for example edge connectors whereby the sensors may be placed into a measuring circuit. In a preferred embodiment this is achieved by making spacer 1 shorter than palladium supporting sheets 14, 15 and by making one sheet 15 of shorter length than the other 14. This forms a socket region 20 having contact areas 21, 22 electrically connected with the working and counter electrodes respectively. A simple tongue plug having corresponding engaging conduct surfaces can then be used for electrical connection. Connectors of other form may be devised.

Chemicals for use in the cell may be supported on the cell electrodes or walls, may be supported on an independent support contained within the cell or may be self-supporting.

In one embodiment, chemicals for use in the cell are printed onto the palladium surface of the electrode immediately after step 1 at which stage the freshly-deposited palladium is more hydrophilic. For example, a solution containing 0.2 molar potassium ferricyanide and 1% by weight of glucose oxidase dehydrogenase may be printed on to the palladium surface. Desirably, the chemicals are printed only in the areas which will form a wall of the cell and for preference the chemicals are printed on the surface by means of an ink jet printer. In this manner, the deposition of chemicals may be precisely controlled. If desired, chemicals which are desirably separated until required for use may be printed respectively on the first and second electrodes. For example, a GOD/ferrocyanide composition can be printed on one electrode and a buffer on the other. Although it is highly preferred to apply the chemicals to the electrodes prior to assembly into a cell, chemicals may also be introduced into the cell as a solution after step 6 or step 8 by pipette in the traditional manner and the solvent subsequently is removed by evaporation or drying. Chemicals need not be printed on the cell wall or the electrodes and may instead be impregnated into a gauze, membrane, non-woven fabric or the like contained within, or filling, the cavity (eg inserted in cell 11 prior to steps 6 or 7). In another embodiment the chemicals are formed into a porous mass which may be introduced into the cell as a pellet or granules. Alternatively, the chemicals maybe introduced as a gel.

In a second embodiment of the invention a laminate 21 is first made from a strip 14 as obtained in step 5 adhesively sandwiched between two strips 7 as obtained from step 3. Laminate 20 is substituted for sheet 1 in step 5 and assembled with electrodes as in steps 6 and 7.

Figure 15:
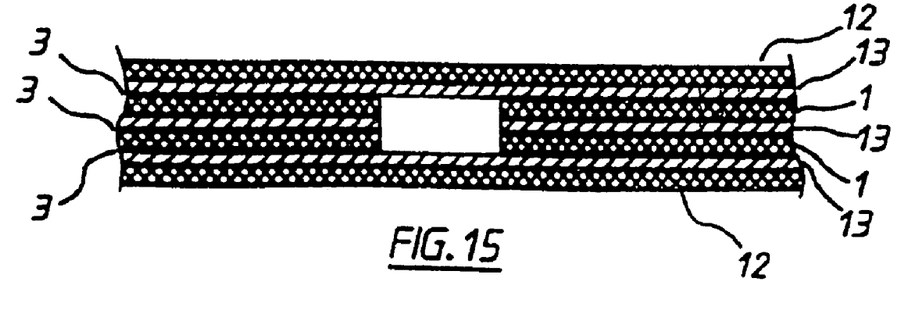
FIG. 15 shows a scrap portion of a second embodiment of the invention in enlarged section.

There is thus obtained a cell as shown in FIG. 15 which differs from that of FIGS. 9 to 11 in that the cell has an annular electrode disposed between the first and second electrode. This electrode can for example be used as a reference electrode.

It will be understood that in mass production of the cell, the parts may be assembled as a laminate on a continuous line. For example, a continuous sheet 1 of PET could be first punched and then adhesive could be applied continuously by printing on the remaining sheet. Electrodes (pre-printed with chemical solution and dried) could be fed directly as a laminate onto the adhesive coated side. Adhesive could then be applied to the other side of the punched core sheet and then the electrode could be fed as a laminate onto the second side.

The adhesive could be applied as a hot melt interleaving film. Alternatively, the core sheet could first be adhesive coated and then punched.

By drying chemicals on each electrode prior to the gluing step the electrode surface is protected from contamination.

Although the cell has been described with reference to Mylar® and Melinex® PET, other chemically inert and electrically resistive materials may be utilised and other dimensions chosen. The materials used for spacer sheet 1 and-for supporting the reference and counter electrodes may be the same or may differ one from the other. Although the invention has been described with reference to palladium electrodes, other metals such as platinum, silver, gold, copper or the like may be used and silver may be reacted with a chloride to form a silver/silver chloride electrode or with other halides. The electrodes need not be of the same metal.

Although the use of heat activated adhesives has been described, the parts may be assembled by use of hot melt adhesives, fusible laminates and other methods.

The dimensions of the sensor may readily be varied according to requirements.

While it is greatly preferred that the electrodes cover the cell end openings, in other embodiments (not illustrated) the electrodes do not entirely cover the cell end openings. In that case it is desirable that the electrodes be in substantial overlying registration.

Preferred forms of the invention in which the electrodes cover the apertures of cell 11 have the advantages that the electrode area is precisely defined simply by punching hole 11. Furthermore the electrodes so provided are parallel, overlying, of substantially the same area, and are substantially or entirely devoid of "edge" effects.

Although in the embodiments described each sensor has one cell cavity, sensors may be provided with two or more cavities. For example, a second cavity may be provided with a predetermined quantity of the analyte and may function as a reference cell.

As will be apparent to those skilled in the art from the teaching herein contained, a feature of one embodiment herein described may be combined with features of other embodiments herein described or with other embodiments described in our co-pending application. Although the sensor has been described with reference to palladium electrodes and a GOD/ferrocyanide chemistry, it will be apparent to those skilled in the art that other chemistries, and other materials of construction may be employed without departing from the principles herein taught.

What is claimed is:

1. A biosensor for use in determining a concentration of a component in an aqueous liquid sample, the biosensor comprising:
    (a) an electrochemical cell, the electrochemical cell comprising a first electrically resistive substrate having a first thin layer of a first electrically conductive material on a first face, a second electrically resistive substrate having a second thin layer of a second electrically conductive material on a second face, the substrates being disposed with the first electrically conductive material facing the second electrically conductive material and being separated by a sheet comprising an aperture, the wall of which aperture cooperates with the electrically conductive materials to define a cell wall, and wherein the aperture defines a working electrode area in the cell, the cell further comprising a sample introduction aperture whereby the aqueous liquid sample may be introduced into the cell, (b) a socket region having a first contact area in electrical communication with the first thin layer of the first electrically conductive material on the first electrically resistive substrate and a second contact area in electrical communication with the second thin layer of the second electrically conductive material on the second electrically resistive substrate, wherein the socket region extends the full width of the first and second electrically resistive substrates, and the first and second electrically resistive substrates have lengths that are different from one another in the socket region; and (c) a measuring circuit, the measuring circuit being electrically connectable with the electrochemical cell by engaging with the socket region.

2. The biosensor of claim 1, wherein the measuring circuit comprises a tongue plug having conductive surfaces that correspond to a shape of the first and second electrically resistive substrates in the socket region such that the tongue plug can be electrically connected to the socket region.

3. The biosensor of claim 1, wherein at least one of the first electrically conductive material and the second electrically conductive material comprises a metal.

4. The biosensor of claim 3, wherein the metal comprises a sputter coated metal.

5. The biosensor of claim 1, wherein the aqueous liquid sample comprises blood.

6. The biosensor of claim 1, wherein the component comprises glucose.

7. The biosensor of claim 1, wherein the measuring circuit comprises an automated instrument for detecting an electrical signal from the electrochemical cell and relating the electrical signal to the concentration of the component in the aqueous liquid sample.

8. A biosensor for use in determining a concentration of a component in an aqueous liquid sample, the biosensor comprising:

(a) a thin layer electrochemical cell, the cell comprising:

(i) an electrically resistive sheet comprising an aperture wherein the aperture defines a working electrode area in the cell;

(ii) a first electrode layer covering the aperture on a first side of the sheet;

(iii) a second electrode layer covering the aperture on a second side of the sheet;

(iv) a passage for admission into the aperture of the aqueous liquid sample; and (v) a socket region for receiving a tongue plug, the socket region having a first contact area in electrical communication with the first electrode layer and a second contact area in electrical communication with the second electrode layer, wherein the socket region extends the full width of the first and second electrode layers and the first and second electrode layers have lengths that are different from one another in the socket region; and (b) a measuring circuit.

9. The biosensor of claim 8, wherein the electrochemical cell is adapted to electrically connect with the measuring circuit.

10. The biosensor of claim 8, wherein the measuring circuit comprises a tongue plug having conductive surfaces that correspond to a shape of the first and second electrode layers in the socket region such that the tongue plug can be electrically connected to the socket region.

11. The biosensor of claim 8, wherein the aqueous liquid sample comprises blood.

12. The biosensor of claim 8, wherein the component comprises glucose.

13. The biosensor of claim 8, wherein the measuring circuit comprises an automated instrument for detecting an electrical signal from the electrochemical cell and relating the electrical signal to the concentration of the component in the aqueous liquid sample.

14. The biosensor of claim 8, wherein the cell comprises a substantially flat strip having a thickness, the strip having at least two lateral edges, and wherein the passage for admission into the aperture comprises a notch through the entire thickness of the strip in at least one of the lateral edges thereof.

* * * * *